US009632020B2

(12) United States Patent
Hunt et al.

(10) Patent No.: US 9,632,020 B2
(45) Date of Patent: Apr. 25, 2017

(54) NON-LINEAR OPTICAL ELLIPSOMETRY FOR SURFACE MONITORING AND CHARACTERIZATION

(71) Applicant: The Boeing Company, Huntington Beach, CA (US)

(72) Inventors: Jeffrey H. Hunt, Thousand Oaks, CA (US); John H. Belk, St. Louis, MO (US)

(73) Assignee: THE BOEING COMPANY, Chicago, IL (US)

( * ) Notice: Subject to any disclaimer, the term of this patent is extended or adjusted under 35 U.S.C. 154(b) by 289 days.

(21) Appl. No.: 14/520,940

(22) Filed: Oct. 22, 2014

(65) Prior Publication Data
US 2016/0116396 A1    Apr. 28, 2016

(51) Int. Cl.
G01N 21/21    (2006.01)
G01N 21/84    (2006.01)
(Continued)

(52) U.S. Cl.
CPC ....... *G01N 21/211* (2013.01); *G01N 21/8422* (2013.01); *G01N 21/8806* (2013.01); *G01N 21/94* (2013.01); *G01N 2021/213* (2013.01); *G01N 2021/8848* (2013.01); *G01N 2201/06113* (2013.01)

(58) Field of Classification Search
CPC ...... G01N 21/21; G01N 21/211; G01N 21/23; G01N 21/8422; G01N 21/958; G01N 2021/8427; G01N 2021/8433; G01N 2021/8438; G01N 2021/8848; G01N 2021/212; G01N 2021/213; G01N 2021/214; G01N 2021/215; G01N 2021/216; G01N 2021/217; G01N 2021/218; G01J 3/447; G01J 4/00; G01J 4/02; G01J 4/04; G01J 2004/001; G01J 2004/002; G01J 2004/004; G01J 2004/005; G01J 2004/007; G01J 2004/008; G01J 5/58; G01J 2005/586; G01B 11/02; G01B 11/06; G01B 11/0616; G01B 11/0625; G01B 11/0633; G01B 11/0641; G01B 11/065; G01B 11/26; G01B 11/27; G01B 11/272
See application file for complete search history.

(56) References Cited

U.S. PATENT DOCUMENTS 5,548,404 A * 8/1996 Kupershmidt ....... G01N 21/211
356/368
7,075,650 B1 * 7/2006 Johs .................... G01N 21/211
356/369
(Continued)

OTHER PUBLICATIONS

Bovino et al., "Nonlinear Ellipsometry by Second Harmonic Generation," Nonlinear Optics, 2012, pp. 117-132, ISBN: 978-953-51-0131-4, InTech, available from: http://www.intechopen.com/books/nonlinearoptics/nonlinear-ellipsometry-by-second-harmonic-generation.
(Continued)

*Primary Examiner* — Gordon J Stock, Jr.
(74) *Attorney, Agent, or Firm* — Coats & Bennett, PLLC

(57) ABSTRACT

The present disclosure relates to monitoring, evaluating and interrogating material surfaces using second-order nonlinear optical ellipsometry for surface monitoring and characterization.

21 Claims, 4 Drawing Sheets

(51) Int. Cl.
*G01N 21/94* (2006.01)
*G01N 21/88* (2006.01)

(56) References Cited

U.S. PATENT DOCUMENTS

| | | | |
|---|---|---|---|
| 7,304,305 B2 | 12/2007 | Hunt | |
| 7,336,359 B1* | 2/2008 | Simpson | G01N 21/211 |
| | | | 356/364 |
| 7,492,455 B1* | 2/2009 | Johs | G01J 3/02 |
| | | | 356/364 |
| 8,736,838 B2 | 5/2014 | Herzinger | |
| 8,743,368 B2 | 6/2014 | Meyers et al. | |
| 9,404,854 B2* | 8/2016 | Hunt | G01N 21/3581 |
| 2010/0155524 A1* | 6/2010 | Maganas | B64C 21/10 |
| | | | 244/39 |
| 2010/0311949 A1* | 12/2010 | Akkus | A61L 27/24 |
| | | | 530/356 |

OTHER PUBLICATIONS

ODA, "Uncooled Bolometer-type Terahertz Focal Plane Array and Camera for Real-Time Imaging," C.R. Physique, vol. 11, 2010, pp. 496-509.

\* cited by examiner

NON-LINEAR OPTICAL ELLIPSOMETRY FOR SURFACE MONITORING AND CHARACTERIZATION

TECHNOLOGICAL FIELD

The present disclosure relates to monitoring, evaluating and interrogating material surfaces. More particularly the present disclosure relates to monitoring material surfaces using second-order nonlinear optical ellipsometry for surface monitoring and characterization.

BACKGROUND

Ellipsometry involves causing a spectroscopic beam of electromagnetic radiation, in a known state of polarization, to interact with a sample, such as, for example, a substrate material surface, at an angle of incidence with respect to a substrate material surface, and often in a plane of incidence. A plane of incidence comprises both a normal plane to a surface being interrogated and the locus of the electromagnetic radiation beam. Changes in the polarization state of the beam that occur as a result of beam interaction with a substrate material surface are indicative of the structure and composition of the substrate material system. Ellipsometry further involves proposing a mathematical model of the ellipsometry system and the substrate material surface being interrogated. Experimental data is obtained from the beam by collecting the beam at a detector after beam incidence at a substrate material surface.

In non-linear optical, or wave mixing processes, outputs are produced at sum, difference or harmonic frequencies of the input beam(s), otherwise equivalently referred to as signal(s). Second order non-linear optics, or three wave mixing involves combining two input signals to produce one output signal at one of the combined frequencies. The use of second order nonlinear optical surface spectroscopy to examine physical properties of a material surface is known. However, practical constraints on such known methods have impeded progress on the material evaluation and characterization below the surface of a material under inspection.

Composite materials such as fiberglass, Kevlar, and carbon fiber are increasingly being used as structural components in aircraft because of their high strength-to-weight ratios, improved performance, reduced corrosion, etc. compared with other known structural materials. However, composites can be weakened by various defects and stress during their life cycle. Routine maintenance of composites requires complicated inspection and repair techniques.

One particular aspect of desired surface analysis and interrogation is the need to characterize the alignment of surface molecules occurring at a substrate material surface and/or any non-native species that may be present on the surface, (e.g. contaminants in the material itself, or contaminants associated with material processing and manufacturing, etc.). Non-invasive, on-site surface analysis has proven difficult, even under optimum environmental conditions, while often constraining implementation of the known diagnostics to a manufacturing environment. Once a material is processed into a finished product, use of known surface interrogation techniques, systems and apparatuses for monitoring the condition of surfaces in the field to assess surface conditions, such as, for example, material fatigue, stress, etc., has not been possible, or has yielded unreliable and non-repeatable data.

SUMMARY

According to one aspect, the present disclosure is directed to a method for evaluating a substrate material surface by providing a substrate having a substrate material surface, positioning a plurality of optical sources, wherein each optical source has or is in communication with a polarization controller and each optical source emits radiation as optical source input signals. Each optical source input signal is directed from an optical source to a polarization controller. The optical source input signals are mixed at a predetermined area of the substrate material surface to create a combined output signal emanating from the substrate material surface. At least a portion of the output signal is directed from the predetermined location on the substrate material surface, and a detector is positioned at a predetermined location, with the detector having, or being in communication with a polarization controller and a polarization rotator. At least a portion of the output signal is directed from the predetermined area on the substrate material surface to the polarization controller and polarization rotator to null the output signal. At least a portion of the output signal is then directed from the polarization rotator to the detector. The detector detects at least a portion of the output signal that is directed from the predetermined area at the substrate material surface though a polarization rotator and a polarization controller before the output signal proceeds to the detector. Features of the substrate material surface at the molecular level are then characterized, based on the characteristics of the signal received by the detector.

In another aspect, the present disclosure contemplates non-invasive methods, systems and apparatuses for detecting the presence of microscopic particles (e.g. as small as from about 0.1 molecular layer to about 3 molecular layers, and more specifically from about 0.1 molecular layer to about 1.0 molecular layer) on a substrate material surface by providing a substrate material surface, positioning a second order non-linear ellipsometry array having a plurality of optical sources, with each optical source having an optical source polarization control. An optical source input signal is emitted from each optical source, and at least a portion of each optical source input signal is directed at a predetermined area on a substrate material surface. The optical source input beams are mixed at or near the substrate material surface to produce a second order non-linear output signal. A detector is positioned at a predetermined location, with the detector having, or in communication with, a polarization rotator and a polarization controller. At least a portion of the second order non-linear output signal is directed to the polarization rotator and the polarization controller. The polarization of the second order non-linear output signal is altered to a minimum signal of from about 10 seconds of polarization to about 10 degrees of polarization rotation. The altered second order non-linear output signal is directed to the detector to detect the altered second order non-linear output signal. Surface characteristics of the substrate material surface are detected by characterizing the microscopic alignment of material detected at the substrate material surface at depths as small as from about 0.1 to about 1.0 molecular layer.

According to further aspects, the second order non-linear optical ellipsometry array comprises a plurality of optical sources, with each optical source comprising a polarization controller to control an optical input signal.

In a still further aspect, an optical source output signal polarization controller alters an output signal.

In yet another aspect, a polarization rotator is adjusted to null an output signal.

In further aspects, at least one optical source is a laser, with the laser having at least one predetermined emitting frequency, and with the predetermined emitting frequency tuned to a frequency that is substantially equivalent to a surface resonance of a substrate material surface.

In a still further aspect, each optical source input signal interacts with the substrate material surface to produce a modified input signal, such as a sum-frequency generation, a second harmonic generation, etc., and combinations thereof.

In another aspect, the optical source input signal is modified by an optical source polarization controller. The polarization modification of the optical source input beam changes the value of the sum-frequency generation and/or second harmonic generation.

In another aspect, the value of the sum-frequency generation and/or second harmonic generation is altered by an output polarization controller to move a minimum signal of from about 0.5 micron to about 0.1 micron.

In a still further aspect, the polarization rotator re-zeroes, or nulls, the output signal before the output signal impacts the detector.

In a further aspect, the value of the sum-frequency generation and/or second harmonic generation output signal is altered by the polarization control to move a minimum signal of from about 10 seconds of polarization rotation to about 10 degrees of polarization rotation.

In a further aspect, the mixing of the optical source inputs signals emitted from the input source polarization controllers produces a signal that is surface sensitive. Surface sensitivity is understood as relating to the signals predominantly emanating from a first atomic or molecular layer of the substrate material surface; or a distance from the surface (beneath the surface) of about 0.1 to about 1 nanometer.

Further aspects of the disclosure are directed to systems and apparatuses for non-invasively evaluating substrate material molecules at a substrate material surface, the systems and apparatuses having a plurality of optical sources, with each optical source positioned to direct emitted radiation from each optical source as an input signal to a predetermined area on a substrate material surface, and with each optical source having an optical source polarization controller. The input signals combine, or are mixed, at a predetermined area on the substrate material surface to produce an output signal. A detector having, or in communication with, a polarization rotator and polarization controller is positioned at a predetermined location. The detector is positioned to receive at least a portion of the output signal directed to the detector from the predetermined area of the substrate material surface, and the detector detects at least a portion of the output signal directed to the detector from the predetermined area of the substrate material surface. In a further aspect, the value of the sum-frequency generation and/or second harmonic generation output signal is altered by the polarization control to move a minimum signal of from about 10 seconds of polarization rotation to about 10 degrees of polarization rotation. The detector is positioned to receive and detect at least a portion of the output signal directed to the detector from the predetermined area of the substrate material surface to characterize the substrate material surface at a molecular level, based on the characteristics of the output signal received by the detector.

According to a further aspect, the present application is directed to non-invasive systems and apparatuses for detecting the presence of microscopic alignment of molecules on a substrate material surface, the systems and apparatuses having a second order non-linear optical ellipsometry array to detect and characterize microscopic material alignment at a predetermined area on a substrate material surface. The array has a detector comprising, or in communication with, a polarization rotator and polarization controller, with the detector positioned at a predetermined location to receive output signals from the predetermined area on the substrate material surface. In a further aspect, the value of the sum-frequency generation and/or second harmonic generation output signal is altered by the polarization controller to move a minimum signal of from about 10 seconds of polarization rotation to about 10 degrees of polarization rotation.

In further aspects, at least one of the optical sources is a laser having at least one frequency, with the emitting frequency tuned to a frequency that is substantially equivalent to a resonance of the substrate material surface.

In still further aspects, the optical source input signal from each optical source combine with each other and are mixed at or near the substrate material surface to produce an output signal having a modified frequency, such as, for example, sum-frequency generated frequency, a second harmonic generated frequency, etc. and combinations thereof.

In a further aspect, the optical source polarization controller is set to modify each optical source input signal to a minimum optical source input signal.

In another aspect, the optical source input is modified by the optical source polarization controller to change the value of the sum-frequency generation and/or second harmonic generation.

In a still further aspect, the value of the frequency of the sum-frequency generation and/or second harmonic generation is altered by the optical source polarization control to produce an output signal from the substrate material surface having a minimum wavelength of from about 0.1 micron to about 1 micron.

In another aspect, the polarization rotator nulls the output signal before the output signal impacts the detector.

In yet another aspect, the combined optical source inputs are surface sensitive.

In another aspect, the first optical source input signal and the second optical source input signals are directed onto a predetermined area of the substrate material simultaneously or substantially simultaneously.

In further aspect, the present disclosure is directed to apparatuses comprising the systems and methods disclosed herein.

In a still further aspect, the methods, systems and apparatuses of the present disclosure are directed to a vehicle, wherein the vehicle may be an aircraft, with the vehicle comprising a substrate material surface, wherein at least a portion of the substrate material surface is interrogated by positioning a plurality of optical sources, wherein each optical source has or is in communication with a polarization controller and each optical source emits radiation as optical source input signals. Each optical source input signal is directed from an optical source to a polarization controller. The optical source input signals are mixed at a predetermined area of the substrate material surface to create a combined output signal emanating from the substrate material surface. At least a portion of the output signal is directed from the predetermined location on the substrate material surface, and a detector is positioned at a predetermined location, with the detector having, or being in communication with a polarization controller and a polarization rotator. At least a portion of the output signal is directed from the predetermined area on the substrate material surface to the polarization controller and polarization rotator to null the output signal. At least a portion of the output signal is then directed from the polarization rotator to the detector. The detector detects at least a portion of the output signal that is directed from the predetermined area at the substrate material surface though a polarization rotator and a polarization controller before the output signal proceeds to the detector. Features of the substrate material surface at the molecular level are then characterized, based on the characteristics of the signal received by the detector.

In another aspect, the methods, systems and apparatuses of the present disclosure are directed to a vehicle comprising a substrate material surface, wherein the vehicle may be an aircraft, and wherein at least a portion of the substrate material surface is interrogated by detecting the presence of microscopic particles (e.g. as small as from about 0.1 molecular layer to about 3 molecular layers, and more specifically from about 0.1 molecular layer to about 1.0 molecular layer) on a substrate material surface by providing a substrate material surface, positioning a second order non-linear ellipsometry array having a plurality of optical sources, with each optical source having an optical source polarization control. An optical source input signal is emitted from each optical source, and at least a portion of each optical source input signal is directed at a predetermined area on a substrate material surface. The optical source input beams are mixed at or near the substrate material surface to produce a second order non-linear output signal. A detector is positioned at a predetermined location, with the detector having, or in communication with, a polarization rotator and a polarization controller. At least a portion of the second order non-linear output signal is directed to the polarization rotator and the polarization controller. The polarization of the second order non-linear output signal is altered to a minimum signal of from about 10 seconds of polarization to about 10 degrees of polarization rotation. The altered second order non-linear output signal is directed to the detector to detect the altered second order non-linear output signal. Surface characteristics of the substrate material surface are detected by characterizing the microscopic alignment of material detected at the substrate material surface at depths as small as from about 0.1 to about 1.0 molecular layer.

In a further aspect, the vehicle includes, but is not limited to, manned or unmanned objects and structures in an atmospheric or space environment. Contemplated objects include vehicles, such as, for example, aircraft, satellites, rockets, missiles, etc., and therefor include manned and unmanned aircraft, spacecraft, terrestrial vehicles, non-terrestrial vehicles and even surface and sub-surface water-borne marine vehicles, objects and structures.

The methods, systems and apparatuses of the present disclosure provide solutions to the problems of accurately and cost-effectively interrogating and evaluating substrate material surface and sub-surface characteristics including, but not limited to the interrogation and evaluation of chemical composition, homogeneity, heterogeneity, mechanical surface irregularities (including, but not limited to, defects and contamination), crystallographic defects, surface, etc., and combinations thereof.

For the purpose of this disclosure, the terms "area", "location" and "region" are used interchangeably and have equivalent meaning when referring to the substrate material.

For the purpose of this disclosure, the terms "interrogation" and "characterization" are used interchangeably and have equivalent meaning when referring to the substrate material.

For the purpose of this disclosure, the terms "characteristics" and "properties" are used interchangeably and have equivalent meaning when referring to the substrate material.

BRIEF DESCRIPTION OF THE DRAWINGS

Figure 1:
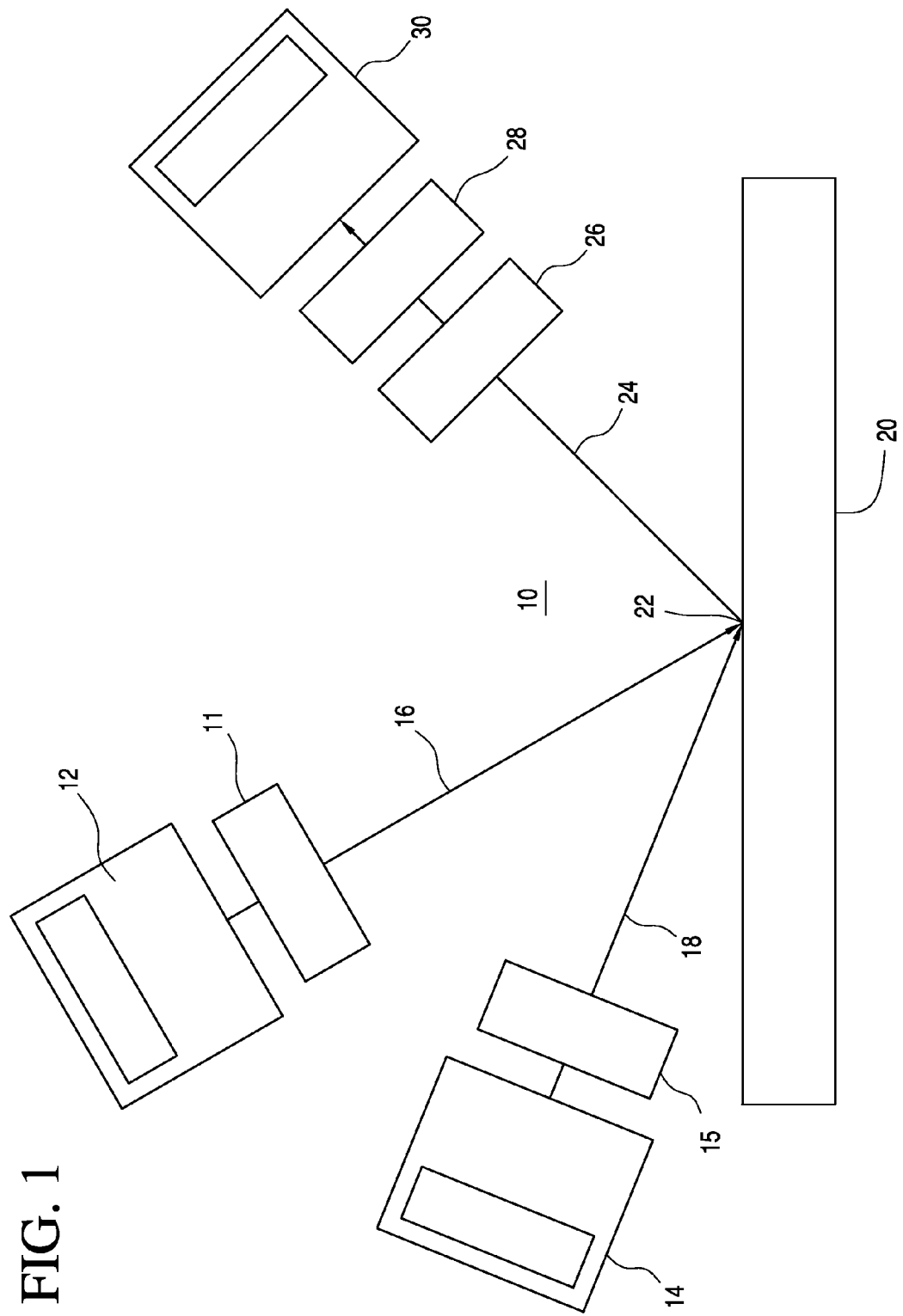
Figure 2:
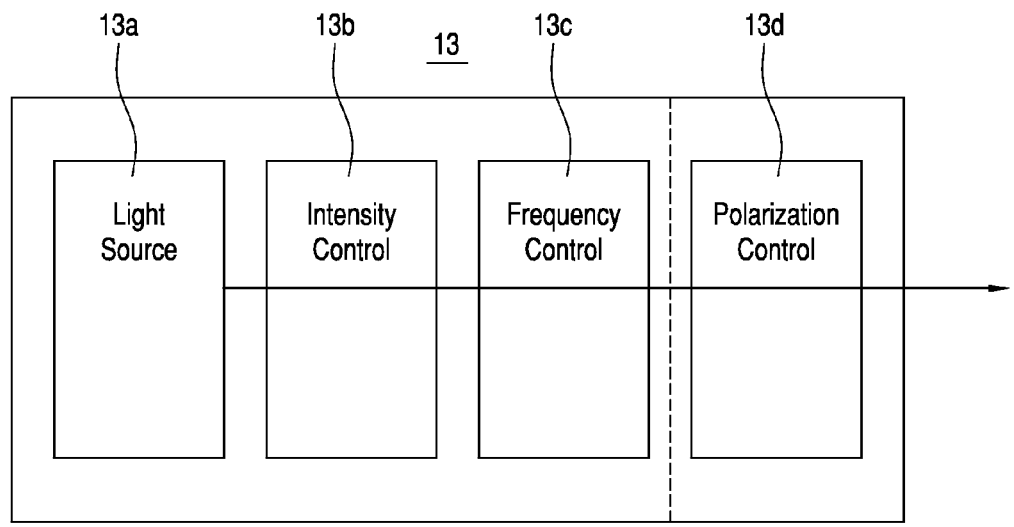
Figure 3:
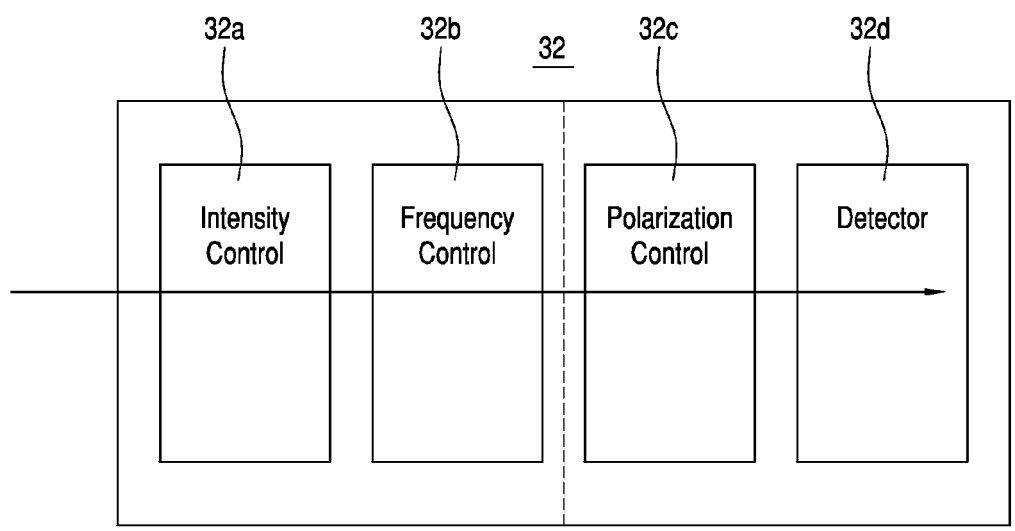
Figure 4:
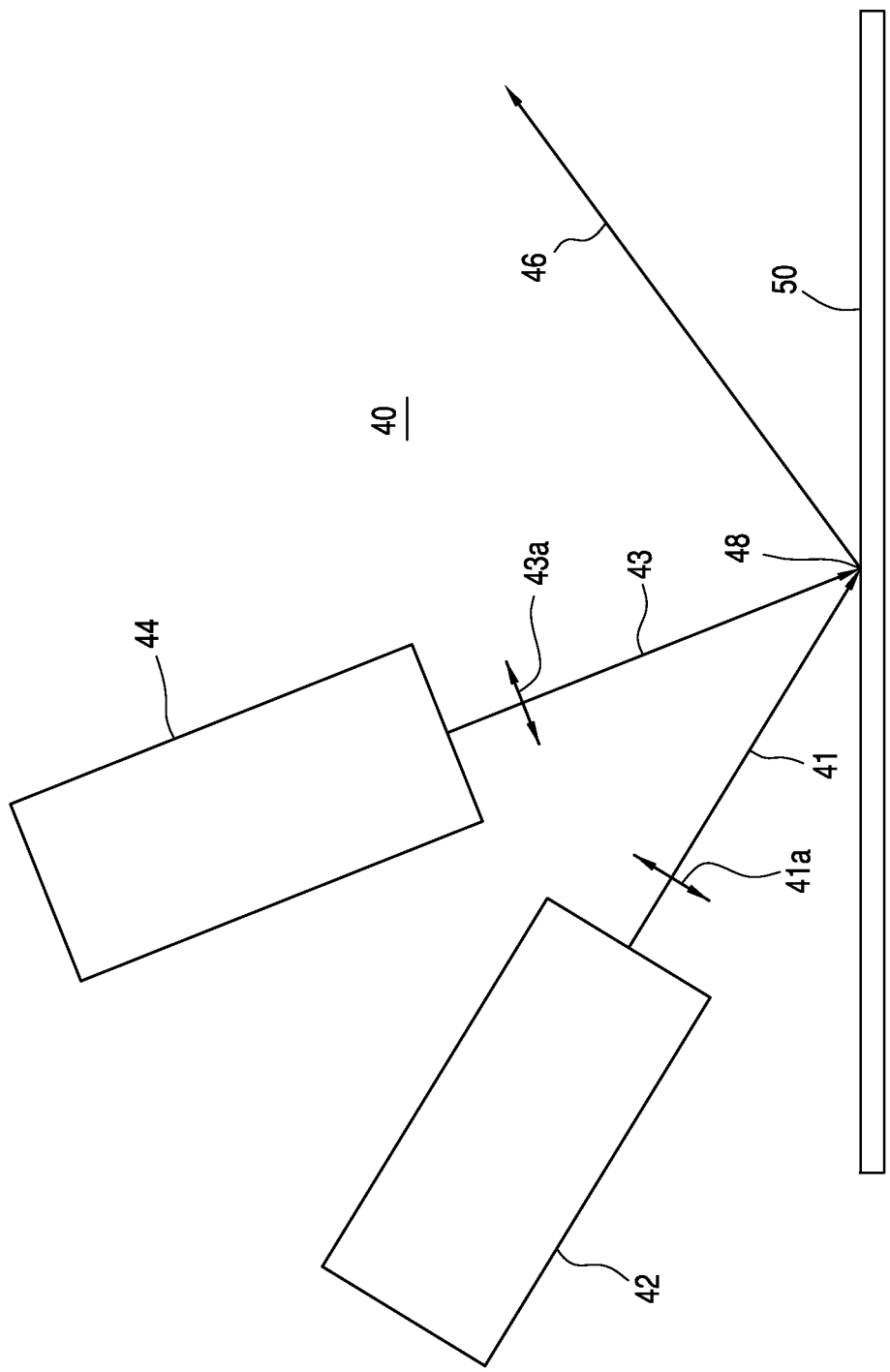

Having thus described variations of the disclosure in general terms, reference will now be made to the accompanying drawings, which are not necessarily drawn to scale, and wherein:

FIG. 1 is a schematic diagram of an aspect of the present disclosure;

FIG. 2 is a schematic diagram of elements in an optical source according to one aspect of the present disclosure;

FIG. 3 is a schematic diagram of elements in a detector according to one aspect of the present disclosure;

FIG. 4 is a schematic diagram of an aspect of the present disclosure; and

Figure 5:
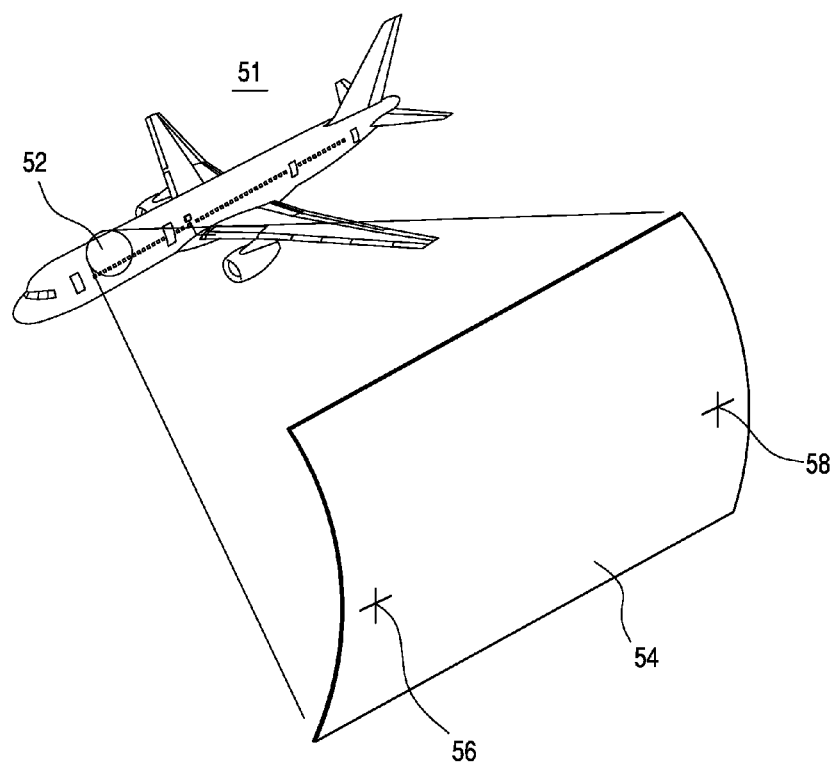

FIG. 5 is a drawing of an aircraft comprising material interrogated by an aspect of the present disclosure.

DETAILED DESCRIPTION

Scalable and repeatable non-invasive surface diagnostic techniques that can be applied in a manufacturing environment are rare and difficult to implement. It is even more difficult to employ such diagnostic techniques that can inspect and characterize substrate material surfaces.

Ellipsometer systems applied to interrogate a substrate material surface typically comprise: a source for emitting a beam of electromagnetic radiation; a polarization element; optionally a compensator element; a substrate material surface to be interrogated; optionally, a second compensator element; a spectroscopic detector element, and, an analyzer element in the detector, or in communication with the detector.

In known ellipsometry methods, the input and output polarization controls and polarizers are adjusted to give a zero strength signal, also referred to as being "nulled". As the surface is modified by the input signals, the polarization in the output will change, such that the output signal will no longer be "zero" (or "nulled"). As a result, the combination of a half wave plate or a quarter wave plate in the output signal detector will be reset to "re-zero", or "re-null" the signal. By "reading" the changes in in signals due to the orientation of half wave and quarter wave plates, and interpreting the signal changes, various properties that changed on the material surface being interrogated may be deduced. However, the presence of attendant signal "noise" has adversely impacted the desired system sensitivities in known ellipsometry techniques and systems.

According to aspects of the present disclosure, the use of non-linear ellipsometry results in the significantly improved characterization of changes in a substrate material surface. While limited similarities exist between known ellipsometry systems and the non-linear ellipsometry methods, systems and apparatuses described herein, significant differences exist between the two systems that yield significantly improved characterization interrogation of a substrate material surface, down to interrogation and characterization at the molecular level. More specifically, according to aspects of the non-linear ellipsometry methods, systems, and apparatuses of the present disclosure, polarization input and output controllers are adjusted to zero out the signal from the substrate material surface being interrogated. As changes occur on the substrate material surface, the signal measured at the output signal detector will be a value above zero. The half wave and quarter wave plates in the output signal detector will then be re-adjusted to re-zero the signal. However, according to aspects of the present disclosure, unlike known ellipsometry systems, the non-linear methods, systems and apparatuses according to aspects of the present disclosure provide non-linear signal mixing that results in an output signal that only emanates from the substrate material surface at the molecular level, thereby significantly improving the sensitivity of the changes occurring at the substrate material surface. This is in strong contrast to known ellipsometry systems wherein signal that emanate from substrate material sub-surfaces, as deep as one wavelength into the sub-surface mix with the substrate material surface output signals. Since known ellipsometry systems comprise signals having a 1 micron wavelength, the known ellipsometry signals will penetrate into the sub-surface to a depth of from 100 to 1000 molecular layers. By contrast, according to aspects of the present disclosure, the non-linear ellipsometry method, systems and apparatuses produce signals from the surface second harmonic generation (SHG) or sum frequency generation (SFG) format and will only penetrate into the subsurface to a depth at most of from about 1 to about 3 molecular layers, and may otherwise only emanate from about 0.1 to about 1.0 molecular surface layer depending upon the substrate material surface being interrogated.

When performing surface SFG or surface SHG, combining multiple electromagnetic signals, there are polarization rules that are derived from a combination of the surface orientation and the molecular orientation of the substrate material surface being interrogated by the incident signals. Such polarization rules concern the molecular symmetry rules in place at the surface being interrogated. The intended signal strengths at each of these surface orientation and molecular orientation combinations have now been calculated based on an analytical evaluation of static orientation. However, according to aspects of the present disclosure, with analytical knowledge of a surface behavior, the input signals of the two input polarizations and the output signal (impacted by an the output polarization controller and a polarization rotator) can be set for a minimum signal level resulting in a commensurate increase in signal sensitivity. As the surface is modified, or as the frequency of an optical source is tuned through a substrate material surface resonance, the signal of SHG or SFG will change (i.e. will move from the desired minimum signal). According to one aspect of the present disclosure, in a manner analogous to linear ellipsometry, a polarization rotator on the output signal side (a polarization rotator positioned in the path of the output signal directed away from the substrate material surface after incidence of the beam on the substrate material surface) is re-zeroed, or re-nulled, thereby re-nulling the signal. Since this is a second order mixing signal, the signal will be surface sensitive. In addition to improving sensitivity, techniques presented according to an aspect of the present disclosure can be used to evaluate the dependence on optical intensity and material resonant behavior down to the molecular level.

An aspect of the present disclosure is therefore directed to the use of second order non-linear optical ellipsometry (SHG or SFG) to evaluate and characterize microscopic material alignment at a substrate material surface. According to aspects of the present disclosure, non-linear optical processes produce signals at the substrate material surface that have now been shown to provide an output signal that is significantly more surface-sensitive and therefore increasingly responsive to modification occurring at the substrate material surface as compared to known linear optical systems.

For the purpose of this disclosure, the terms "area", "location" and "region" are used interchangeably and have equivalent meaning when referring to the substrate material.

For the purpose of this disclosure, the terms "interrogation" and "characterization" are used interchangeably and have equivalent meaning when referring to the substrate material.

The methods, systems and apparatuses of the present disclosure provide solutions to the problems of accurately and cost-effectively interrogating and evaluating substrate material surface and sub-surface characteristics including, but not limited to the interrogation and evaluation of chemical composition, homogeneity, heterogeneity, mechanical surface irregularities (including, but not limited to, defects and contamination), crystallographic defects, surface, etc., and combinations thereof.

According to one aspect, because the optical sources of the present disclosure require diagnostics requiring a non-linear optical source interaction, pulse lasers with desired peak intensities of from about 1 KW/cm$^2$ to about 1 GW/cm$^2$ are contemplated. One contemplated laser source are solid-state lasers, such as, for example, Nd:YAG lasers operating on the 1.064 micron line, or a Nd:YAG laser and a harmonic converter for operation at the second or third harmonic of the fundamental output wavelength. Such a source may operate with a maximum pulse length of about 10 nsec, with the optimal pulse length being about 10 psec. The useful range for the difference frequency is the THz spectrum of from about 0.1 THz to about 100 THz. More complex lasers such as Ti:sapphire lasers are also contemplated. The contemplated lasers are commercially available from sources including Coherent, Spectra-Physics, Melles-Griot, etc.

According to another aspect of the disclosure, the signal collection optics may include a telescope system comprising a plurality of lenses having desired materials and coatings optimized for the sum frequency output wavelength, in the wavelength band from about 0.1 micron to about 1.0 micron. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

FIG. 1 shows a schematic representation of one aspect of the present disclosure. Diagnostic system 10 shows a first optical source 12 and a second optical source 14. FIG. 1 shows one aspect of the disclosure where the first optical polarization control 11 and second optical source polarization control 15 exist as a component that is not physically integrated with first optical source 12 and second optical source 14, respectively. First optical source 12 emits a first tunable optical input signal 16 that is directed through first polarization control 11, with first input signal 16 being then directed onto a predetermined area 22 on a substrate material surface 20 being interrogated. Second optical source 14 emits a second tunable optical beam input signal 18 that is directed through a second polarization control 15, with second input signal 18 being then directed onto a predetermined area 22 on a substrate material surface 20 being interrogated. In one variation, the first and second input signals 16, 18 are directed onto the predetermined area 22 on the substrate material surface being interrogated 20, simultaneously, or substantially simultaneously.

According to the present disclosure, the term "substantially simultaneously" means that the delay in time of two input beam, for example, must be accurate to some fraction of the duration of the pulse length. For example, if 10 ns pulses are used, the delay considered to still be substantially simultaneous should be from about 1 ns to about 1 ps. The first and second optical sources are positioned in a predetermined orientation so that their surface areas of optical illumination overlap at predetermined area 22 on the substrate material surface 20 being interrogated. This positioning may be implemented via a series of refractive and reflective elements. For example, by changing their tilt in two axes, elements in series can propagate a laser beam to any position on a surface. The first and second input signals 16, 18 interact in a predetermined fashion at the predetermined area 22 on substrate material surface 20, such that a combined output signal 24 that is now the sum frequency of the first and second optical sources, is directed away from the preselected area 22 on the substrate material surface 20. The combined output signal from the first optical source 12 and second source 14 is in the range of from about 0.5 to about 0.1. Sum frequency output signal 24 is directed to a polarization rotator 26 in communication with an output polarization control 28, and on to a detector 30.

While the elements present in each optical source may be similar, each optical source may have differing intensities, frequencies and/or different polarization. The frequency control will typically comprise an optical filter to regulate the light that reaches the substrate material surface. The optical filter will also insure that any stray light generated by the optical source is removed, or does not reach the substrate material surface. Such regulation can be accomplished using notch filters, color filters spectrometers or any other frequency selective element alone or in combination, etc.

Polarization controllers will vary but typically comprise two separate optical elements: a polarizer and a polarization-modifying element. The polarizer refers to an element that passes light of one polarization type. A polarizing-modifying element is typically a halfway plate or a quarter plate. A halfway plate is used to rotate the polarization to a desired orientation. A quarter wave plate is used to change polarization from linear to circular or from circular to linear. According to one aspect of the present disclosure, the polarizer is oriented as the last element in a selected array before light leaves the source and proceeds toward the substrate material surface.

As shown in FIG. 2, according to one aspect, the input optics 13 comprise an optical source light source 13a, an optical source intensity controller 13b, an optical source frequency controller 13c, and an optical source polarization controller 13d. According to one aspect of the present disclosure, it is understood that the optical source 13 and its components 13a, 13b, 13c and 13d shown in FIG. 2 may represent an optical source having the components to be found in both the first optical source 12 and the second optical source 14 (with the understanding that the input optics typically comprise one polarization controller). It is understood that the order of the components relative to one another may be altered, as desired, depending on desired signal mixing effects.

FIG. 3 shows one aspect of the disclosure, showing a detection component 32 for detecting output signal 24. Detection component comprises an intensity controller 32a, a frequency controller 32b, a polarization controller 32c, and a detector 32d. It is understood that the order of the components relative to one another may be altered as desired depending on desired signal mixing effects.

The first and second optical sources 12, 14 include a visible input in optical communication with associated input optics. According to one aspect, the optical sources comprise a narrow frequency bandwidth visible pulse laser, such as, for example a pulsed diode laser, a continuous wave diode laser, a pulsed solid state laser, or a continuous wave solid state laser.

As stated above, the detector 30 is understood to further comprise components necessary to receive and process the signals generated as the sum frequency output signal 24 (created by the combined optical source inputs 16 and 18) that is directed together from a substrate surface being interrogated to the detector. Such further components include those shown in FIG. 3; namely, an intensity controller and a frequency controller, otherwise referred equivalently to as a frequency discriminator.

According to one contemplated variation, within the detector 30, signal collection optics receive the combined output signal 24 from the first and second optical sources that is directed from the substrate material surface being interrogated. A frequency controller (otherwise referred to as a wavelength or frequency discriminator) is first encountered by the output signal. The signal collection optics direct the propagation of the sum frequency output signals so that a collected sum frequency output signal is formed after propagation through the signal collection optics. The signal collection optics may be either refractive or reflective optics that act to control the divergence of the light coming from the surface being interrogated so that as much of the light signal as possible is collected for analysis. According to a further variation, an optical detector converts the collected optical light signal to an electronic signal, thus monitoring the intensity of the sum frequency output signal as a function of surface characterization. An electronic signal analyzer analyzes the electron signal for providing surface-sensitive spectroscopic characterizations. According to one aspect, the electronic signal analyzer may be, for example, a computer with suitable internal electronics, and hardware, software, etc., to implement the appropriate mathematical algorithms to interpret the received electronic signals. It is further understood that the electronic signal analyzer may be integrated into, or may be located remotely from, the detector 30.

According to one aspect, the presence of contamination on a surface being interrogated will change the spectroscopic response of the surface. Since the amount of light generated at the sum frequency output wavelength will depend upon the surface spectroscopy, appropriate interpretation of the output signal provides a means to monitor the existence and amount of contamination present on the surface.

FIG. 4 shows a further aspect of the present disclosure. System 40 comprises a first optical source 42 having a first input signal 41 and a second optical source 44 having a second signal 43 directed to a predetermined area 48 on substrate material surface 50. Arrows 41a and 43a indicate the polarization of the respective input signals. When the polarization is in the so-called "P" configuration, the polarization is in the plane of the page. Alternately, when the polarization is in the "S" configuration, the polarization is perpendicular to the page. The output signal 46 from the substrate material surface may have combinations of P and S configurations depending on what occurs at the material substrate surface. Polarization of the output signal 46 is not set in the same way that the input signal polarizations are set. However, the polarizer at the detector array (not shown) can be set to only evaluate P or S polarizations as desired, in the output signal 46 coming from the predetermined area 48 of the substrate material surface 50 being interrogated. Therefore, with two possible polarizations (P and S) from each optical source, and two possible polarization readings (by the detector) from the output signal, there are a number of allowable combinations. For example, one input can be set to P and the other input set to S, with the detector's polarizer set to read P polarization. Depending on the substrate material surface characteristic being evaluated and interrogated, any number of such polarization combinations can be selected.

As stated above, according to one aspect, the presence of contamination on a surface being interrogated will change the spectroscopic response of the surface. Since the amount of light generated at the second harmonic frequency output wavelength will depend upon the substrate material surface and substrate material sub-surface spectroscopy, appropriate interpretation of the electronic signal provides a means to monitor the amount of contamination present at the material substrate surface and material substrate sub-surface.

According to one aspect, the optical source may comprise a Nd:YAG laser operating on the 1.064 micron line, or a Nd:YAG laser and a harmonic converter for operation at the second or third harmonic of the fundamental output wavelength. It may operate with a maximum pulse length of about 10 nsec, with the optimal pulse length being about 10 ps. According to further aspects, the optical sources comprise tunable visible input capabilities including steering apparatuses that may comprise mirrors aligned so that their surface normal are non-coplanar, with the mirrors' reflectances being optimized for an output wavelength of the tunable visible laser. Polarizers may be used that are operative in the visible range so that an output wavelength is p or s polarized with the polarization referenced to the surface to be interrogated. In one aspect, a spot shaping apparatus is used that may include a series of lenses for creating a predetermined and controlled spot size on the surface to be interrogated. The lenses may be transparent in the visible range.

The output wavelength discriminator preferably includes an iris, a filter in communication with the iris for passing output sum frequency wavelength, and a polarizer in optical communication with the filter aligned to detect either the p or s polarization and referenced to the surface where the sum frequency output signal is generated.

According to another aspect of the disclosure, the signal collection optics may include a telescope system comprising a plurality of lenses having desired materials and coatings optimized for the sum frequency output wavelength, in the wavelength band from about 0.1 micron to about 1.0 micron. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

While aspects of the present disclosure's material inspection and material interrogation methods, systems and apparatuses can be employed without restriction to particular materials that are used for particular applications, such methods, systems and apparatuses are deemed useful to inspect and otherwise interrogate materials designed to be used on the exterior or interior of atmospheric and aerospace vehicles and other objects designed for use in space or other upper atmosphere environments (such as, for example, hypersonic vehicles). Further contemplated uses abound where exposure to extreme high and cold temperatures are required. Indeed, materials having any required need for sustainable, reusable uses would find benefit from the methods, systems and apparatuses disclose herein, including, but not limited to hypersonic manned and unmanned vehicles and objects in an atmospheric or space environment. Contemplated objects include, but are not limited to, for example, aircraft, satellites, rockets, missiles, etc. and therefore include manned and unmanned aircraft and spacecraft, and also contemplate terrestrial, non-terrestrial, surface and sub-surface water-borne vehicles and objects.

FIG. 5 is a drawing of a vehicle, and, in particular, an aircraft 51. Fuselage panel 54 having a substrate material surface is shown, in an enlarged configuration, as being located at the region of the fuselage at location 52. The marks shown as "+" 56, 58 represent locations on the substrate material surface and sub-surface of fuselage panel 54 that may be interrogated according to methods, systems and apparatuses of the present disclosure. While the drawing shows an aircraft with a portion of fuselage identified, it is understood that the methods, systems and apparatuses of the present disclosure contemplate use with any material substrate surface of any material that can be used anywhere in the construction of any vehicle, such as, for example an aircraft, including the interior, exterior or locations there between.

While the preferred variations and alternatives of the present disclosure have been illustrated and described, it will be appreciated that various changes and substitutions can be made therein without departing from the spirit and scope of the disclosure. Accordingly, the scope of the disclosure should only be limited by the accompanying claims and equivalents thereof.

We claim:

1. A method for non-invasively evaluation a substrate material surface comprising the steps of:
    positioning a first optical source and a second optical source wherein each optical source emits an optical source input signal, with at least one optical source polarization control in communication with each optical source;
    directing each optical source input signal from each optical source to a respective polarization control;
    directing each optical source input signal from the respective optical source polarization control to a predetermined area on a substrate comprising a substrate material surface;
    mixing the optical source input signals at the predetermined area on the substrate material surface to produce a combined output signal;
    positioning a detector at a predetermined location, said detector in communication with polarization rotator and a polarization controller;
    directing at least a portion of the output signal from the predetermined area on the substrate material surface to the polarization controller and polarization rotator to null the output signal; and
    directing at least a portion of the output signal from the polarization rotator to the detector;
    detecting at least a portion of the output signal that is directed from the predetermined area on the substrate material surface to the detector; and
    characterizing features of the predetermined area on the substrate material surface at a molecular level based on characteristics of the output signal received by the detector.

2. The method of claim 1, wherein each optical source is a laser.

3. The method of claim 1, wherein each optical source emits an input signal at a predetermined frequency, with each frequency tuned to a frequency that is substantially equivalent to a substrate material surface resonance.

4. The method of claim 3, wherein each optical sourced input signal interacts with the substrate material surface to produce a modified input signal selected from the group consisting of: a sum-frequency generation, a second harmonic generation, and combinations thereof.

5. The method of claim 4, wherein each optical source input signal is modified by the optical source polarization control to change the value of a frequency of the sum-frequency generation or second harmonic generation.

6. The method of claim 5, wherein the value of the frequency of the sum-frequency generation or second harmonic generation is altered by an output polarization controller to move to a minimum signal wavelength value of from about 0.5 micron to about 0.1 micron.

7. The method of claim 1, wherein the output signal polarization rotator nulls the output signal before the output signal impacts the detector.

8. The method of claim 1, wherein the output signal is altered by the polarization controller to move a minimum signal of from about 10 seconds of polarization rotation to about 10 degrees of polarization rotation.

9. The method of claim 1, wherein the mixing of the optical source inputs emitted from the optical source input polarization controls produces a signal that is surface sensitive.

10. A non-invasive method for detecting the presence of microscopic particles on a substrate material surface comprising the steps of:
    positioning a second order non-linear optical ellipsometry array having a plurality of optical sources, with each optical source comprising an optical source polarization control;
    emitting an optical source input signal from each optical source;
    directing at least a portion of each optical source input signal at a predetermined area on a substrate material surface;
    mixing the optical source input signals at or near the substrate material surface to produce a second order non-linear output signal;
    positioning a detector at a predetermined location, said detector in communication with a polarization rotator and a polarization controller;
    directing at least a portion of the second order non-linear output signal to the polarization rotator;
    altering the polarization of the second order non-linear output signal to move a minimum signal of from about 10 seconds of polarization rotation to about 10 degrees of polarization rotation;
    directing the altered second order non-linear output signal to the detector;
    detecting the altered second order non-linear output beam; and
    characterizing microscopic material alignment of material detected at the predetermined area on the substrate material surface from a depth of from about 0.1 to about 1 molecular layer.

11. The method of claim 10, wherein the second order non-linear optical ellipsometry array comprises a plurality of optical sources, each optical source comprising a polarization controller to control an optical source input signal.

12. The method of claim 10, wherein the polarization rotator is adjusted to null an output signal.

13. A system for non-invasively evaluating substrate material surface molecules at a substrate material surface comprising:
    a plurality of optical sources, each optical source positioned to direct emitted radiation from each optical source as an input signal to a predetermined area on a substrate material surface, wherein each optical source has an optical source polarization control and the input signals combine at the predetermined area on the substrate material surface to produce an output signal; and
    a detector positioned at a predetermined location, said detector comprising a polarization controller and a polarization rotator, with said detector positioned to receive at least a portion of the output signal directed to the detector from the predetermined area of the substrate material surface, and detect at least a portion of the output signal directed to the detector from the predetermined area on the substrate material surface.

14. The system of claim 13, wherein at least one of the optical sources is a laser.

15. The system of claim 14, wherein the laser has at least one emitting frequency, with the emitting frequency tuned to a frequency that is substantially equivalent to a substrate material surface resonance.

16. The system of claim 13, wherein each optical source input signal from each of the optical sources are combined with each other at or near the substrate material surface to produce the output signal, said output signal having a modified frequency selected from the group consisting of: a sum-frequency generated frequency, a second harmonic generated frequency, and combinations thereof.

17. The system of claim 15, wherein the optical source polarization controller modifies each optical source input signal to a minimum optical source input signal.

18. The system of claim 16, wherein each optical source input signal is modified by the polarization controller to change the value of a frequency of the sum-frequency generation or second harmonic generation.

19. The system of claim 18, wherein the value of the frequency of the sum-frequency generation or second harmonic generation is altered by the polarization control to produce an output signal having a minimum wavelength of from about 0.1 micron to about 1.0 micron.

20. The system of claim 13, wherein the polarization rotator nulls the output signal before the output signal impacts the detector.

21. The system of claim 13, wherein the combined optical source input signals are surface sensitive.

* * * * *